US009297744B2

United States Patent
Zeng et al.

(10) Patent No.: US 9,297,744 B2
(45) Date of Patent: Mar. 29, 2016

(54) DEVICE AND METHOD FOR MEASURING PHASE RETARDATION DISTRIBUTION AND FAST AXIS AZIMUTH ANGLE DISTRIBUTION IN REAL TIME

(71) Applicant: Shanghai Institute of Optics And Fine Mechanics, Chinese Academy of Sciences, Shanghai (CN)

(72) Inventors: Aijun Zeng, Shanghai (CN); Longhai Liu, Shanghai (CN); Linglin Zhu, Shanghai (CN); Huijie Huang, Shanghai (CN)

(73) Assignee: Shanghai Institute of Optics And Fine Mechanics, Chinese Academy of Sciences, Shanghai (CN)

( * ) Notice: Subject to any disclaimer, the term of this patent is extended or adjusted under 35 U.S.C. 154(b) by 50 days.

(21) Appl. No.: 14/455,860

(22) Filed: Aug. 8, 2014

(65) Prior Publication Data

US 2014/0347665 A1  Nov. 27, 2014

Related U.S. Application Data

(63) Continuation-in-part of application No. PCT/CN2012/000990, filed on Jul. 23, 2012.

(30) Foreign Application Priority Data

Jun. 15, 2012  (CN) .......................... 2012 1 0199435

(51) Int. Cl.
*G01J 4/00* (2006.01)
*G01N 21/21* (2006.01)
(Continued)

(52) U.S. Cl.
CPC . *G01N 21/21* (2013.01); *G01J 9/00* (2013.01); *G01M 11/02* (2013.01); *G01J 2004/005* (2013.01); *G01N 2021/216* (2013.01)

(58) Field of Classification Search
CPC . G01N 21/21; G01N 2021/216; G01M 11/02; G01J 9/00; G01J 2004/005; G01J 4/04; G01J 4/00

See application file for complete search history.

(56) References Cited

U.S. PATENT DOCUMENTS

| 6,816,261 B2* | 11/2004 | Patel ....................... G01J 3/447 356/364 |
| 2006/0187452 A1 | 8/2006 | Wang |
| 2012/0092669 A1 | 4/2012 | Fiolka et al. |

FOREIGN PATENT DOCUMENTS

| CN | 200710178950.3 | 5/2008 |
| CN | 101319958 A | 12/2008 |

(Continued)

OTHER PUBLICATIONS

Tsung-Chih Yu et al., "Full-Field and Full-Range Sequential Measurement of the Slow Axis Angle and Phase Retardation of Linear Birefringent Material," Applied Optics, vol. 48, pp. 4568-4576 (2009).

(Continued)

*Primary Examiner* — Kara E Geisel
*Assistant Examiner* — Rufus Phillips
(74) *Attorney, Agent, or Firm* — Manni Li; Mei & Mark LLP

(57) ABSTRACT

Device and method for measuring phase retardation distribution and fast axis azimuth angle distribution of birefringence sample in real time. The device consists of a collimating light source, a circular polarizer, a diffractive beam-splitting component, a quarter-wave plate, an analyzer array, a charge coupled device (CCD) image sensor and a computer with an image acquisition card. The method can measure the phase retardation distribution and the fast axis azimuth angle distribution of the birefringence sample in real time and has large measurement range. The measurement result is immune to the light-intensity fluctuation of the light source.

8 Claims, 1 Drawing Sheet

(51) Int. Cl.
*G01M 11/02* (2006.01)
*G01J 9/00* (2006.01)

(56) References Cited

FOREIGN PATENT DOCUMENTS

| CN | 101504329 A | 8/2009 |
| CN | 102175430 A | 9/2011 |

OTHER PUBLICATIONS

Han, Jie et al., "Real-Time Spatial Polarization Decoding Technology Based on Two-Dimensional Grating and Analyzer Arra," Chinese Journal of Scientific Instrument, vol. 31, No. 3, pp. 507-511 (Mar. 2011).

* cited by examiner

DEVICE AND METHOD FOR MEASURING PHASE RETARDATION DISTRIBUTION AND FAST AXIS AZIMUTH ANGLE DISTRIBUTION IN REAL TIME

CROSS-REFERENCE AND RELATED APPLICATIONS

The subject application is a continuation-in-part of PCT international application PCT/CN2012/000990 filed on Jul. 23, 2012, which in turn claims priority on Chinese patent application No. CN 201210199435.4 filed on Jun. 15, 2012. The contents and subject matter of the PCT and Chinese priority applications are incorporated herein by reference.

TECHNICAL FIELD OF THE INVENTION

The subject application relates to polarization measurement, especially one device and method for measuring phase retardation distribution and fast axis azimuth angle distribution of the birefringent component in real time.

BACKGROUND OF THE INVENTION

Birefringent component is widely used in many domains, such as polarized illumination system of immersion lithography, phase shifting interferometry and biological optics. The phase retardation and fast axis azimuth angle are two important parameters of birefringent component. The phase retardation distribution and fast axis azimuth angle distribution of the birefringent component must be acquired when it is used in the immersion lithography polarized illumination system and phase shifting interferometry. So it is of essentiality to precisely measure the phase retardation distribution and fast axis azimuth angle distribution of the birefringent component.

The Chinese Laid-Open Patent Application No. 200710178950.3 discloses a method and system of precisely measuring the optical phase retardation. By using an optical modulator in the optical setup, the modulated polarized light is generated. After filtering the measurement signals, the measurement of DC zero value is transferred to the measurement of AC zero value. By precisely judging the position of the extreme point, the phase retardation can be measured. But this method cannot measure the fast axis azimuth angle of the sample and the phase retardation distribution in real time.

Tsung-Chih Yu et al. in a paper entitled "Full-field and full-range sequential measurement of the slow axis angle and phase retardation of linear birefringent materials", Applied Optics, Vol. 48, p. 4568(2009), discloses a method of measuring the phase retardation distribution and fast axis azimuth angle distribution of birefringent materials by using heterodyne interferometry method and three-step time-domain phase shifting method. This method needs to change part of the light path to measure the phase retardation distribution and fast axis azimuth angle distribution in step by step and uses the time-domain phase shifting technology, thus it is not feasible for measuring the phase retardation distribution and fast axis azimuth angle distribution in real time.

SUMMARY OF THE INVENTION

The purpose of the subject invention is to overcome the shortages of the above technology. One method and device of measuring the phase retardation distribution and fast axis azimuth angle distribution in real time is proposed. The measured result is immune to the fluctuation of the initial light intensity and this method has large measuring range.

The subject application provides a device for measuring the phase retardation distribution and fast axis azimuth angle distribution in real time, which is composed of a collimating light source, a circular polarizer, a diffractive component, a quarter-wave plate, an analyzer array, a CCD image sensor and a computer equipped with an image acquisition card. Said analyzer array is composed of four analyzers whose polarization directions successively increase by 45°. They are respectively named as the first analyzer, the second analyzer, the third analyzer and the fourth analyzer. The positions of the above components are as follows:

Said quarter-wave plate is located in the same path with said first analyzer. And the angle between the fast axis of said quarter-wave plate and the transmission direction of said first analyzer is 45° or 135°. Light emitted from said collimating light source passes through said circular polarizer and said diffractive component and then is split into four sub-beams. One sub-beam passes through said quarter-wave plate and is then analyzed by said first analyzer. The other three sub-beams are directly analyzed by said second analyzer, said third analyzer and said fourth analyzer, respectively. The output port of said image sensor is connected to the input port of said computer. The faucet for the measuring sample is set between said circular polarizer and said diffractive component.

Said collimating light source is a He—Ne laser, solid state laser or semiconductor laser.

Said circular polarizer is made of birefringent crystal, birefringent film or micro optical element.

Said diffractive component is a Quadrature Amplitude grating, Quadrature Phase grating or Dammann grating. The diffractive component can split the incident beam into four sub beams with the same light intensity.

Said quarter wave plate is a crystal wave plate, prismatic wave plate, film wave plate or composite wave plate.

Said first analyzer, second analyzer, third analyzer and fourth analyzer are all the polarizer whose extinction ratio is better than $10^{-3}$.

The method of measuring the phase retardation distribution and fast axis azimuth angle distribution in real time contains the following steps.

①  Insert the measuring sample into said faucet between said circular polarizer and said diffractive component, then adjust the light beam to let it perpendicularly pass through the measuring sample.

②  Turn on said collimating light source, said CCD image sensor and said computer. Said CCD image sensor receives an image formed by said four sub-beams and then transmits it to said computer. Said computer segregates said image into four sub-images. Then the four said sub-images are all pixelated and established a same coordinate system, respectively. The measuring sample is also matrixed and established a coordinate system which is the same with that of the sub-image. The intensity values in said four sub-images corresponding to the measured matrix unit (x, y) of the measuring sample are $I_1(x, y)$, $I_2(x, y)$, $I_3(x, y)$ and $I_4(x, y)$. By calculating said intensity values, the phase retardation and fast axis azimuth angle of said matrix unit (x, y) of the measuring sample are obtained. So the phase retardation distribution and the fast axis azimuth angle distribution of the measuring sample can be obtained by processing said four sub-images.

Said computer processing said sub-images contains the following steps in detail:

When the polarization direction of said first analyzer is 45° relative to the fast axis of said quarter wave plate, said computer will perform the steps ③, ④.

③ Said computer processes the intensity values $I_1(x, y)$, $I_2(x, y)$, $I_3(x, y)$ and $I_4(x, y)$ corresponding to said matrix unit $(x, y)$ as follows:

$$V_1(x, y) = \sin(\delta(x, y))\sin(2\theta(x, y)) = \frac{2I_1(x, y)}{I_1(x, y) + I_3(x, y)} - 1,$$

$$V_2(x, y) = \sin(\delta(x, y))\cos(2\theta(x, y)) = \frac{2I_4(x, y)}{I_1(x, y) + I_3(x, y)} - 1,$$

$$V_3(x, y) = \cos(\delta(x, y)) = 1 - \frac{2I_2(x, y)}{I_1(x, y) + I_3(x, y)}.$$

Wherein $\delta(x, y)$ is the retardation of said matrix unit $(x, y)$, and $\theta(x, y)$ is the fast axis azimuth angle of said matrix unit $(x, y)$. Then the retardation $\delta(x, y)$ can be calculated in the range of 0°~180° as follows:

when $\sqrt{V_1^2(x,y)+V_2^2(x,y)} \leq V_3(x,y)$, the $\delta(x,y)$=arc sin $(\sqrt{V_1^2(x,y)+V_2^2(x,y)})$, when $\sqrt{V_1^2(x,y)+V_2^2(x,y)} > |V_3(x,y)|$, the $\delta(x,y)$=arc cos$(V_3(x,y))$, when $\sqrt{V_1^2(x,y)+V_2^2(x,y)} < -V_3(x,y)$, the $\delta(x,y)$=180°− arc sin$(\sqrt{V_1^2(x,y)+V_2^2(x,y)})$.

The fast axis azimuth angle $\theta(x, y)$ can be calculated in the range of −90°~90° as follows:

when $V_2(x,y)<0$ & $V_1(x,y) \leq 0$, the $$\theta(x, y) = \frac{1}{2}\arctan\left(\frac{V_1(x, y)}{V_2(x, y)}\right) - 90°,$$

when $V_2(x,y) > 0$, the $$\theta(x, y) = \frac{1}{2}\arctan\left(\frac{V_1(x, y)}{V_2(x, y)}\right),$$

when $V_2(x,y)<0$ & $V_1(x,y)>0$, the $$\theta(x, y) = \frac{1}{2}\arctan\left(\frac{V_1(x, y)}{V_2(x, y)}\right) + 90°.$$

④ Sequentially change the coordinate values x and y of said matrix unit $(x, y)$ and its corresponding intensity values $I_1(x, y)$, $I_2(x, y)$, $I_3(x, y)$ and $I_4(x, y)$, and then repeat step ③. When the entire matrix units of said measuring sample are calculated, its phase retardation distribution and the fast axis azimuth angle distribution can be obtained.

When the polarization direction of said first analyzer is 135° relative to the fast axis azimuth angle of said quarter wave plate, said computer will perform the steps ⑤, ⑥.

⑤ Said computer processes the intensity values $I_1(x, y)$, $I_2(x, y)$, $I_3(x, y)$ and $I_4(x, y)$ corresponding to said matrix unit $(x, y)$ as follows:

$$V_1(x, y) = \sin(\delta(x, y))\sin(2\theta(x, y)) = \frac{2I_2(x, y)}{I_2(x, y) + I_4(x, y)} - 1,$$

$$V_2(x, y) = \sin(\delta(x, y))\cos(2\theta(x, y)) = 1 - \frac{2I_3(x, y)}{I_2(x, y) + I_4(x, y)},$$

$$V_3(x, y) = \cos(\delta(x, y)) = \frac{2I_1(x, y)}{I_2(x, y) + I_4(x, y)} - 1.$$

Then the retardation $\delta(x, y)$ can be calculated in the range of 0°~180° as follows:

when $\sqrt{V_1^2(x,y)+V_2^2(x,y)} \leq V_3(x,y)$, the $\delta(x,y)$=arc sin $(\sqrt{V_1^2(x,y)+V_2^2(x,y)})$, when $\sqrt{V_1^2(x,y)+V_2^2(x,y)} > |V_3(x,y)|$, the $\delta(x,y)$=arc cos$(V_3(x,y))$, when $\sqrt{V_1^2(x,y)+V_2^2(x,y)} < -V_3(x,y)$, the $\delta(x,y)$=180°− arc sin$(\sqrt{V_1^2(x,y)+V_2^2(x,y)})$.

The fast axis azimuth angle $\theta(x, y)$ can be calculated in the range of −90°~90° as follows:

when $V_2(x,y)<0$ & $V_1(x,y) \leq 0$, the $$\theta(x, y) = \frac{1}{2}\arctan\left(\frac{V_1(x, y)}{V_2(x, y)}\right) - 90°,$$

when $V_2(x,y) > 0$, the $$\theta(x, y) = \frac{1}{2}\arctan\left(\frac{V_1(x, y)}{V_2(x, y)}\right),$$

when $V_2(x,y)<0$ & $V_1(x,y)>0$, the $$\theta(x, y) = \frac{1}{2}\arctan\left(\frac{V_1(x, y)}{V_2(x, y)}\right) + 90°.$$

⑥ Sequentially change the coordinate values x and y of said matrix unit $(x, y)$ and its corresponding intensity values $I_1(x, y)$, $I_2(x, y)$, $I_3(x, y)$ and $I_4(x, y)$, and then repeat step ⑤. When the entire matrix units of said measuring sample are calculated, its phase retardation distribution and the fast axis azimuth angle distribution will be obtained.

Comparing with the previous technology, the technical effect of this invention contains:

1. This invention can measure the phase retardation distribution and fast axis azimuth angle distribution in real time. The light intensity distributions of the four sub-beams are the functions of the phase retardation distribution and fast axis azimuth angle distribution of the measuring sample. The four sub-beams are simultaneously detected by the CCD image sensor and processed at high speed by the computer, thus the phase retardation distribution and fast axis azimuth angle distribution can be obtained in real time.

2. Fluctuation of the initial light intensity will not affect the measured results. The initial light intensity is eliminated during calculation, thus the measured phase retardation distribution and fast axis azimuth angle distribution of the measuring sample is immune to the initial light intensity.

3. The phase retardation and fast axis azimuth angle are of wide measurement range. Using the intensity values of the four sub-beams, the sine and cosine function of the phase retardation and fast axis azimuth angle can be calculated. Utilizing these two functions, the phase retardation can be precisely calculated in the range of 0°~180° and the fast axis azimuth angle can be precisely calculated in the range of −90°~90°.

DETAILED DESCRIPTION OF THE INVENTION

The invention is further explained in combination with the embodiments and the accompanying diagrams, but the protection scope of the invention should not be limited by it.

Example 1

Figure 1:
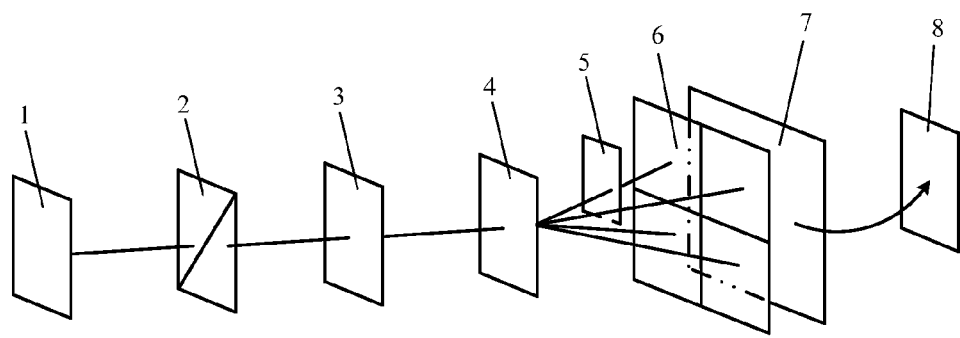
FIG. 1 illustrates the diagram to measure the phase retardation distribution and the fast axis azimuth angle distribution in real time.

The diagram of measuring the phase retardation distribution and the fast axis azimuth angle distribution in real time is illustrated in FIG. 1. The device of measuring the phase retardation distribution and fast axis azimuth angle distribution in real time is composed of collimating light source 1, circular polarizer 2, diffractive component 4, quarter wave plate 5, analyzer array 6, CCD image sensor 7 and computer 8. Light emitted from the collimating light source 1 successively passes through the circular polarizer 2 and the diffractive component 4 and then is split into four sub-beams. One sub-beam passes through the quarter wave plate 5 and then is analyzed by one analyzer of the analyzer array 6, while the other three sub-beams are directly analyzed by the other three analyzers of the analyzer array 6 without passing through the quarter wave plate 5. The CCD image sensor 7 is connected to the computer 8 through electronics. The faucet for the measuring sample 3 is set between the circular polarizer 2 and the diffractive component 4.

The collimating light source 1 is a He—Ne laser.

The circular polarizer 2 is made of calcite crystal and quartz crystal, whose extinction ratio is better than $10^{-3}$.

The diffractive component 4 is a Dammann Grating which can split the incident beam into four plus or minus one-order sub-beams, whose light intensity is equal.

The quarter wave plate 5 is a zero-order standard quartz quarter wave plate, which is located in one sub-beam's path generated by diffractive component 4.

Figure 2:
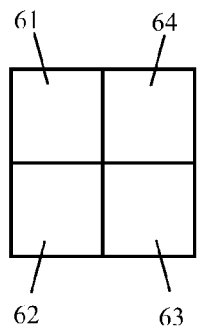
FIG. 2 illustrates the diagram of the analyzer array.

The diagram of the analyzer array 6 is illustrated in FIG. 2. It is composed of first analyzer 61, second analyzer 62, third analyzer 63 and fourth analyzer 64. Their polarization direction angles successively increase by 45° and their extinction ratios are all better than $10^{-3}$. The quarter wave plate 5 is located in the same path with the first analyzer 61. The polarization directions of the first analyzer 61, the second analyzer 62, the third analyzer 63 and the fourth analyzer 64 are respectively 45°, 90°, 135° and 0° relative to the fast axis of the quarter wave plate 5.

The computer 8 is the computer equipped with an image acquisition card.

The method of measuring the phase retardation distribution and fast axis azimuth angle distribution in real time features that it contains the following steps.

① Insert the measuring sample 3 into the faucet between the circular polarizer 2 and the diffractive component 4, and then adjust the beam to let it perpendicularly pass through the measuring sample 3;

② Turn on the collimating light source 1, the CCD image sensor 7 and the computer 8.

The CCD image sensor 7 receives an image formed by said four sub-beams and then transmits it to the computer 8. The computer 8 segregates said image into four sub-images. Then the four said sub-images are all pixelated and established a same coordinate system, respectively. The measuring sample 3 is also matrixed and established a coordinate system which is the same with that of the sub-image. The intensity values in said four sub-images corresponding to the measured matrix unit (x, y) of the measuring sample are $I_1(x, y)$, $I_2(x, y)$, $I_3(x, y)$ and $I_4(x, y)$;

③ The computer 8 processes the intensity values $I_1(x, y)$, $I_2(x, y)$, $I_3(x, y)$ and $I_4(x, y)$ corresponding to the matrix unit (x, y) of the measuring sample 3 as follows:

$$V_1(x, y) = \sin(\delta(x, y))\sin(2\theta(x, y)) = \frac{2I_1(x, y)}{I_1(x, y) + I_3(x, y)} - 1,$$

$$V_2(x, y) = \sin(\delta(x, y))\cos(2\theta(x, y)) = \frac{2I_4(x, y)}{I_1(x, y) + I_3(x, y)} - 1,$$

$$V_3(x, y) = \cos(\delta(x, y)) = 1 - \frac{2I_2(x, y)}{I_1(x, y) + I_3(x, y)}.$$

The retardation δ(x, y) of the matrix unit (x, y) can be calculated in the range of 0°~180°.

When $\sqrt{V_1^2(x,y)+V_2^2(x,y)} \leq V_3(x,y)$, the δ(x,y)=arc sin $(\sqrt{V_1^2(x,y)+V_2^2(x,y)})$, when $\sqrt{V_1^2(x,y)+V_2^2(x,y)} > |V_3(x,y)|$, the δ(x,y)=arc cos $(V_3(x,y))$, when $\sqrt{V_1^2(x,y)+V_2^2(x,y)} \leq -V_3(x,y)$, the δ(x,y)=180°−arc sin$(\sqrt{V_1^2(x,y)+V_2^2(x,y)})$.

The fast axis azimuth angle θ(x, y) of the matrix unit (x, y) can be calculated in the range of −90°~90°.

When $V_2(x,y)<0$ & $V_1(x,y)\leq 0$, the $$\theta(x, y) = \frac{1}{2}\arctan\left(\frac{V_1(x, y)}{V_2(x, y)}\right) - 90°,$$

when $V_2(x,y)>0$, the $$\theta(x, y) = \frac{1}{2}\arctan\left(\frac{V_1(x, y)}{V_2(x, y)}\right),$$

when $V_2(x,y)<0$ & $V_1(x,y)>0$, the $$\theta(x, y) = \frac{1}{2}\arctan\left(\frac{V_1(x, y)}{V_2(x, y)}\right) + 90°.$$

④ Sequentially change the coordinate values x and y of said matrix unit (x, y) and its corresponding intensity values $I_1(x, y)$, $I_2(x, y)$, $I_3(x, y)$ and $I_4(x, y)$, and then repeat step ③. When the entire matrix units of said measuring sample are calculated, its phase retardation distribution and the fast axis azimuth angle distribution will be obtained.

The principle in detail of this invention is explained as follows.

The Jones Vector E of the circularly polarized light emitted from the circular polarizer can be expressed as $$E = \frac{E_0}{\sqrt{2}}\begin{bmatrix} 1 \\ i \end{bmatrix}, \quad (1)$$

wherein $E_0$ is the amplitude of the circularly polarized light.

The Jones Matrix $J_S$ of the matrix unit (x, y) of the measuring sample 3 can be expressed as $$J_s = \begin{bmatrix} \cos\frac{\delta(x,y)}{2} - i\sin\frac{\delta(x,y)}{2}\cos 2\theta(x,y) & -i\sin\frac{\delta(x,y)}{2}\sin 2\theta(x,y) \\ -i\sin\frac{\delta(x,y)}{2}\sin 2\theta(x,y) & \cos\frac{\delta(x,y)}{2} + i\sin\frac{\delta(x,y)}{2}\cos 2\theta(x,y) \end{bmatrix}, \quad (2)$$

wherein $\delta(x, y)$ and $\theta(x, y)$ are respectively the phase retardation and the fast axis azimuth angle of the matrix unit (x, y) of the measuring sample 3. The Jones Matrixes $J_P$ of the first analyzer 61, the second analyzer 62, the third analyzer 63 and the forth analyzer 64 all can be expressed as $$J_P = \begin{bmatrix} \cos^2\alpha & \sin\alpha\cos\alpha \\ \sin\alpha\cos\alpha & \sin^2\alpha \end{bmatrix}, \quad (3)$$

wherein $\alpha$ is the polarization direction angles of the analyzers. The Jones Matrix $J_Q$ of the quarter wave plate 5 can be expressed as $$J_Q = \begin{bmatrix} 1 & 0 \\ 0 & i \end{bmatrix}. \quad (4)$$

After directly analyzed by the second analyzer 62, the third analyzer 63 and the fourth analyzer 64 without passing through the quarter wave plate 5, the Jones Vectors $E_1(x, y)$ of three sub-beams all can be expressed as $$E_1(x,y) = J_P J_S E. \quad (5)$$

After passing through the quarter wave plate 5 and then analyzed by the first analyzer 61, the Jones Matrix $E_2(x, y)$ of one sub-beam can be expressed as $$E_2(x,y) = J_P J_Q J_S E. \quad (6)$$

When the Jones Matrix $E_1(x, y)$ or $E_2(x, y)$ is multiplied by its conjugate transposed matrix, the intensity values $I_1(x, y)$, $I_2(x, y)$, $I_3(x, y)$, $I_4(x, y)$ of the four sub-beams corresponding to the matrix unit (x, y) of the sample 3 can be expressed as $$I_1(x,y) = I_0(1 - \cos(\delta(x,y))), \quad (7)$$

$$I_2(x,y) = I_0(1 - \sin(\delta(x,y))\sin(2\theta(x,y))), \quad (8)$$

$$I_3(x,y) = I_0(1 + \sin(\delta(x,y))\cos(2\theta(x,y))), \quad (9)$$

$$I_4(x,y) = I_0(1 + \sin(\delta(x,y))\sin(2\theta(x,y))). \quad (10)$$

From equations (7)~(10), it can be deduced that $$V_1(x, y) = \sin(\delta(x, y))\sin(2\theta(x, y)) = \frac{2I_4(x, y)}{I_2(x, y) + I_4(x, y)} - 1, \quad (11)$$

$$V_2(x, y) = \sin(\delta(x, y))\cos(2\theta(x, y)) = \frac{2I_3(x, y)}{I_2(x, y) + I_4(x, y)} - 1, \quad (12)$$

$$V_3(x, y) = \cos(\delta(x, y)) = 1 - \frac{2I_1(x, y)}{I_2(x, y) + I_4(x, y)}. \quad (13)$$

Then when $\sqrt{V_1^2(x,y) + V_2^2(x,y)} \leq V_3(x,y)$, the $\delta(x,y)=\arcsin(\sqrt{V_1^2(x,y) + V_2^2(x,y)})$, (14)

when $\sqrt{V_1^2(x,y) + V_2^2(x,y)} > |V_3(x,y)|$, the $\delta(x,y)=\arccos(V_3(x,y))$, (15)

when $\sqrt{V_1^2(x,y) + V_2^2(x,y)} \leq -V_3(x,y)$, the $\delta(x,y)=180°-\arcsin(\sqrt{V_1^2(x,y) + V_2^2(x,y)})$. (16)

When $V_2(x,y)<0 \& V_1(x,y)\leq 0$, the $$\theta(x, y) = \frac{1}{2}\arctan\left(\frac{V_1(x, y)}{V_2(x, y)}\right) - 90°, \quad (17)$$

when $V_2(x,y)>0$, the $$\theta(x, y) = \frac{1}{2}\arctan\left(\frac{V_1(x, y)}{V_2(x, y)}\right), \quad (18)$$

when $V_2(x,y)<0 \& V_1(x,y)>0$, the $$\theta(x, y) = \frac{1}{2}\arctan\left(\frac{V_1(x, y)}{V_2(x, y)}\right) + 90°. \quad (19)$$

y using equations (14)~(19), the $\delta(x, y)$ distribution can be measured in the range of 0°~180° and $\theta(x, y)$ distribution can be measured in the range of −90°~90°.

Example 2

The difference between embodiment 2 and embodiment 1 is that the polarization directions of the first analyzer 61, the second analyzer 62, the third analyzer 63 and the fourth analyzer 64 are 135°, 0°, 45° and 90° relative to the fast axis of the quarter wave plate 5. And the corresponding data processing steps are also different.

③ The computer 8 processes the intensity values $I_1(x, y)$, $I_2(x, y)$, $I_3(x, y)$ and $I_4(x, y)$ corresponding to the matrix unit (x, y) of the measuring sample 3 as follows:

$$V_1(x, y) = \sin(\delta(x, y))\sin(2\theta(x, y)) = \frac{2I_2(x, y)}{I_2(x, y) + I_4(x, y)} - 1,$$

-continued $$V_2(x, y) = \sin(\delta(x, y))\cos(2\theta(x, y)) = 1 - \frac{2I_3(x, y)}{I_2(x, y) + I_4(x, y)},$$

$$V_3(x, y) = \cos(\delta(x, y)) = \frac{2I_1(x, y)}{I_2(x, y) + I_4(x, y)} - 1.$$

The retardation $\delta(x, y)$ of the matrix unit $(x, y)$ can be calculated in the range of $0 \sim 180°$.

When $\sqrt{V_1^2(x,y)+V_2^2(x,y)} \leq V_3(x,y)$, the $\delta(x,y)$=arc sin $(\sqrt{V_1^2(x,y)+V_2^2(x,y)})$, when $\sqrt{V_1^2(x,y)+V_2^2(x,y)} > |V_3(x,y)|$, the $\delta(x,y)$=arc cos($V_3(x,y)$), when $\sqrt{V_1^2(x,y)+V_2^2(x,y)} < -V_3(x,y)$, the $\delta(x,y)=180°-$ arc sin($\sqrt{V_1^2(x,y)+V_2^2(x,y)}$).

The fast axis azimuth angle $\theta(x, y)$ of the matrix unit $(x, y)$ can be calculated in the range of $-90° \sim 90°$.

When $V_2(x,y)<0 \& V_1(x,y) \leq 0$, the $$\theta(x, y) = \frac{1}{2}\arctan\left(\frac{V_1(x, y)}{V_2(x, y)}\right) - 90°,$$

when $V_2(x,y)>0$, the $$\theta(x, y) = \frac{1}{2}\arctan\left(\frac{V_1(x, y)}{V_2(x, y)}\right),$$

when $V_2(x,y)<0 \& V_1(x,y)>0$, the $$\theta(x, y) = \frac{1}{2}\arctan\left(\frac{V_1(x, y)}{V_2(x, y)}\right) + 90°.$$

④ Sequentially change the coordinate values x and y of said matrix unit $(x, y)$ and its corresponding intensity values $I_1(x, y)$, $I_2(x, y)$, $I_3(x, y)$ and $I_4(x, y)$, and then repeat step ③. When the entire matrix units of said measuring sample are calculated, its phase retardation distribution and the fast axis azimuth angle distribution will be obtained.

The principle of this invention is explained as follows.

The Jones Vector E of the circularly polarized light emitted from the circular polarizer can be expressed as $$E = \frac{E_0}{\sqrt{2}}\begin{bmatrix} 1 \\ i \end{bmatrix},\quad (20)$$

wherein $E_0$ is the amplitude of the circularly polarized light. The Jones Matrix $J_S$ of the matrix unit $(x, y)$ of the measuring sample 3 can be expressed as $$J_s = \begin{bmatrix} \cos\frac{\delta(x, y)}{2} - & -i\sin\frac{\delta(x, y)}{2}\sin2\theta(x, y) \\ i\sin\frac{\delta(x, y)}{2}\cos2\theta(x, y) & \\ -i\sin\frac{\delta(x, y)}{2}\sin2\theta(x, y) & \cos\frac{\delta(x, y)}{2} + i\sin\frac{\delta(x, y)}{2}\cos2\theta(x, y) \end{bmatrix},\quad (21)$$

wherein $\delta(x, y)$ and $\theta(x, y)$ are respectively the phase retardation and the fast axis azimuth angle of the matrix unit $(x, y)$ of the sample 3. The Jones Matrixes $J_P$ of the first analyzer 61, the second analyzer 62, the third analyzer 63 and the forth analyzer 64 all can be expressed as $$J_P = \begin{bmatrix} \cos^2\alpha & \sin\alpha\cos\alpha \\ \sin\alpha\cos\alpha & \sin^2\alpha \end{bmatrix},\quad (22)$$

wherein $\alpha$ is the polarization direction angles of the analyzers. The Jones Matrix $J_Q$ of the quarter wave plate 5 can be expressed as $$J_Q = \begin{bmatrix} 1 & 0 \\ 0 & i \end{bmatrix}.\quad (23)$$

After directly analyzed by the second analyzer 62, the third analyzer 63 and the fourth analyzer 64 without passing through the quarter wave plate 5, the Jones Vectors $E_1(x, y)$ of three sub-beams all can be expressed as $$E_1(x,y) = J_P J_S E. \quad (24)$$

After passing through the quarter wave plate 5 and then analyzed by the first analyzer 61, the Jones Matrix $E_2(x, y)$ of one sub-beam can be expressed as $$E_2(x,y) = J_P J_Q J_S E. \quad (25)$$

When the Jones Matrix $E_1(x, y)$ or $E_2(x, y)$ is multiplied by its conjugate transposed matrix, the intensity values $I_1(x, y)$, $I_2(x, y)$, $I_3(x, y)$, $I_4(x, y)$ of the four sub-beams corresponding to the matrix unit $(x, y)$ of the measuring sample 3 can be expressed as $$I_1(x,y) = I_0(1+\cos(\delta(x,y))), \quad (26)$$

$$I_2(x,y) = I_0(1+\sin(\delta(x,y))\sin(2\theta(x,y))), \quad (27)$$

$$I_3(x,y) = I_0(1-\sin(\delta(x,y))\cos(2\theta(x,y))), \quad (28)$$

$$I_4(x,y) = I_0(1-\sin(\delta(x,y))\sin(2\theta(x,y))). \quad (29)$$

From equations (26)~(29), it can be deduced that $$V_1(x, y) = \sin(\delta(x, y))\sin(2\theta(x, y)) = \frac{2I_2(x, y)}{I_2(x, y) + I_4(x, y)} - 1, \quad (30)$$

$$V_2(x, y) = \sin(\delta(x, y))\cos(2\theta(x, y)) = 1 - \frac{2I_3(x, y)}{I_2(x, y) + I_4(x, y)}, \quad (31)$$

$$V_3(x, y) = \cos(\delta(x, y)) = \frac{2I_1(x, y)}{I_2(x, y) + I_4(x, y)} - 1. \quad (32)$$

Then when $\sqrt{V_1^2(x,y)+V_2^2(x,y)} \leq V_3(x,y)$, the $\delta(x,y)$=arc sin($\sqrt{V_1^2(x,y)+V_2^2(x,y)}$), (33)

when $\sqrt{V_1^2(x,y)+V_2^2(x,y)} > |V_3(x,y)|$, the $\delta(x,y)=\arccos(V_3(x,y))$, (34)

when $\sqrt{V_1^2(x,y)+V_2^2(x,y)} < -V_3(x,y)$, the $\delta(x,y)=180°-\arcsin(\sqrt{V_1^2(x,y)+V_2^2(x,y)})$. (35)

When $V_2(x,y)<0 \& V_1(x,y)\leq 0$, the $$\theta(x, y) = \frac{1}{2}\arctan\left(\frac{V_1(x, y)}{V_2(x, y)}\right) - 90°,\qquad(36)$$

when $V_2(x,y)>0$, the $$\theta(x, y) = \frac{1}{2}\arctan\left(\frac{V_1(x, y)}{V_2(x, y)}\right),\qquad(37)$$

when $V_2(x,y)<0 \& V_1(x,y)>0$, the $$\theta(x, y) = \frac{1}{2}\arctan\left(\frac{V_1(x, y)}{V_2(x, y)}\right) + 90°.\qquad(38)$$

By using equations (33)~(38), the $\delta(x, y)$ distribution can be measured in the range of 0°~180° and $\theta(x, y)$ distribution can be measured in the range of −90°~90°.

Experiment results show that this invention can measure the phase retardation distribution and fast axis azimuth angle distribution in real time. The measured results are immune to the fluctuation of the initial intensity. Meanwhile this invention is of wide measurement range.

We claim:

1. A device for measuring the phase retardation distribution and fast axis azimuth angle distribution in real time, comprising
    a collimating light source,
    a circular polarizer,
    a diffractive beam-splitting component,
    a quarter wave plate,
    an analyzer array,
    a CCD image sensor, and
    a computer equipped with an image acquisition card,
    wherein the analyzer array is composed of four analyzers whose polarization direction angles successively increase by 45°, they are respectively named as a first analyzer, a second analyzer, a third analyzer, and a fourth analyzer;
    the quarter wave plate is located in the same path with the first analyzer, and the angle between a fast axis of the quarter wave plate and transmission direction of the first analyzer is 45° or 135°;
    light emitted from the collimating light source passes through the circular polarizer and the diffractive component, and is then split into four sub-beams;
    one sub-beam passes through the quarter wave plate and then is analyzed by the first analyzer, the other three sub-beams are directly analyzed by the second analyzer, the third analyzer, and the fourth analyzer, respectively;
    an output port of the image sensor is connected to an input port of the computer; and
    a faucet for the measuring sample is set between the circular polarizer and the diffractive component.

2. The device for measuring the phase retardation distribution and fast axis azimuth angle distribution in real time of claim 1, wherein the collimating light source is a He—Ne laser, solid state laser, or semiconductor laser.

3. The device for measuring the phase retardation distribution and fast axis azimuth angle distribution in real time of claim 1, wherein the circular polarizer is made of birefringent crystal, birefringent film, or micro optical element.

4. The device for measuring the phase retardation distribution and fast axis azimuth angle distribution in real time of claim 1, wherein the diffractive component is Quadrature Amplitude grating, Quadrature Phase grating or Dammann grating, which splits the incident beam into four sub-beams with the same light intensity.

5. The device for measuring the phase retardation distribution and fast axis azimuth angle distribution in real time of claim 1, wherein the quarter wave plate is a crystal wave plate, prismatic wave plate, film wave plate, or composite wave plate.

6. The device for measuring the phase retardation distribution and fast axis azimuth angle distribution in real time of claim 1, wherein the first analyzer, second analyzer, third analyzer, and fourth analyzer are all the polarizer whose extinction ratio is better than $10^{-3}$.

7. The method for measuring the phase retardation distribution and fast axis azimuth angle distribution in real time of claim 1, comprising
    inserting a measuring sample into the faucet between said circular polarizer and the diffractive component,
    adjusting the light beam to let it perpendicularly pass through the measuring sample,
    forming an image by the four sub-beams,
    receiving the image by the CCD image sensor and transmitting the image to the computer,
    segregating the image into four sub-images in the computer, and processing the four sub-images in the computer to obtain a phase retardation distribution and fast axis azimuth angle distribution of the measuring sample,
    wherein the four sub-images are all pixelated and established a same coordinate system, respectively; the measuring sample is also matrixed and established a coordinate system which is the same with the coordinate system of the sub-image; intensity values in said four sub-images corresponding to the measured matrix unit (x, y) of the measuring sample are $I_1(x, y)$, $I_2(x, y)$, $I_3(x, y)$ and $I_4(x, y)$; calculating said intensity values to obtain the phase retardation and fast axis azimuth angle of said matrix unit (x, y) of the measuring sample.

8. The measurement method of claim 7, wherein the computer processes said sub-images by
    when the polarization direction of the first analyzer is 45° relative to the fast axis of the quarter wave plate, performing steps of (3) and (4) by the computer:
    (3) processing the intensity values $I_1(x, y)$, $I_2(x, y)$, $I_3(x, y)$ and $I_4(x, y)$ corresponding to said matrix unit (x, y) as follows:

$$V_1(x, y) = \sin(\delta(x, y))\sin(2\theta(x, y)) = \frac{2I_1(x, y)}{I_1(x, y) + I_3(x, y)} - 1,$$

$$V_2(x, y) = \sin(\delta(x, y))\cos(2\theta(x, y)) = \frac{2I_4(x, y)}{I_1(x, y) + I_3(x, y)} - 1,$$

$$V_3(x, y) = \cos(\delta(x, y)) = 1 - \frac{2I_2(x, y)}{I_1(x, y) + I_3(x, y)}.$$

wherein δ(x, y) is a retardation of the matrix unit (x, y), and θ(x, y) is a fast axis azimuth angle of the matrix unit (x, y);

calculating the retardation δ(x, y) in a range of 0°~180° as follows:

when $\sqrt{V_1^2(x,y)+V_2^2(x,y)} \le V_3(x,y)$, the δ(x,y)=arc sin $(\sqrt{V_1^2(x,y)+V_2^2(x,y)})$, when $\sqrt{V_1^2(x,y)+V_2^2(x,y)} > |V_3(x,y)|$, the δ(x,y)=arc cos($V_3(x,y)$), when $\sqrt{V_1^2(x,y)+V_2^2(x,y)} \le -V_3(x,y)$, the δ(x,y)=180°− arc sin($\sqrt{V_1^2(x,y)+V_2^2(x,y)}$).

calculating the fast axis azimuth angle θ(x, y) in a range of −90°~90° as follows:

when $V_2(x,y)<0 \& V_1(x,y) \le 0$, the $$\theta(x, y) = \frac{1}{2}\arctan\left(\frac{V_1(x, y)}{V_2(x, y)}\right) - 90°,$$

when $V_2(x,y)>0$, the $$\theta(x, y) = \frac{1}{2}\arctan\left(\frac{V_1(x, y)}{V_2(x, y)}\right),$$

when $V_2(x,y)<0 \& V_1(x,y)>0$, the $$\theta(x, y) = \frac{1}{2}\arctan\left(\frac{V_1(x, y)}{V_2(x, y)}\right) + 90°,$$

and (4) sequentially changing the coordinate values x and y of the matrix unit (x, y) and its corresponding intensities $I_1(x, y)$, $I_2(x, y)$, $I_3(x, y)$ and $I_4(x, y)$, and repeating step (3); and when the entire matrix units of the measuring sample are calculated, its phase retardation distribution and the fast axis azimuth angle distribution are obtained;

when the polarization direction of the first analyzer is 135° relative to the fast axis azimuth angle of the quarter wave plate, performing steps (5) and (6) by the computer:

(5) processing the intensity values $I_1(x, y)$, $I_2(x, y)$, $I_3(x, y)$ and $I_4(x, y)$ corresponding to said matrix unit (x, y) as follows:

$$V_1(x, y) = \sin(\delta(x, y))\sin(2\theta(x, y)) = \frac{2I_2(x, y)}{I_2(x, y) + I_4(x, y)} - 1,$$

$$V_2(x, y) = \sin(\delta(x, y))\cos(2\theta(x, y)) = 1 - \frac{2I_3(x, y)}{I_2(x, y) + I_4(x, y)},$$

$$V_3(x, y) = \cos(\delta(x, y)) = \frac{2I_1(x, y)}{I_2(x, y) + I_4(x, y)} - 1,$$

and calculating the retardation δ(x, y) in a range of 0°~180° as follows:

when $\sqrt{V_1^2(x,y)+V_2^2(x,y)} \ge V_3(x,y)$, the δ(x,y)=arc sin $(\sqrt{V_1^2(x,y)+V_2^2(x,y)})$, when $\sqrt{V_1^2(x,y)+V_2^2(x,y)} > |V_3(x,y)|$, the δ(x,y)=arc cos($V_3(x,y)$), when $\sqrt{V_1^2(x,y)+V_2^2(x,y)} \le -V_3(x,y)$, the δ(x,y)=180°− arc sin($\sqrt{V_1^2(x,y)+V_2^2(x,y)}$); and calculating the fast axis azimuth angle θ(x, y) in a range of −90°~90° as follows:

when $V_2(x,y)<0 \& V_1(x,y) \le 0$, the $$\theta(x, y) = \frac{1}{2}\arctan\left(\frac{V_1(x, y)}{V_2(x, y)}\right) - 90°,$$

when $V_2(x,y)>0$, the $$\theta(x, y) = \frac{1}{2}\arctan\left(\frac{V_1(x, y)}{V_2(x, y)}\right),$$

when $V_2(x,y)<0 \& V_1(x,y)>0$, the $$\theta(x, y) = \frac{1}{2}\arctan\left(\frac{V_1(x, y)}{V_2(x, y)}\right) + 90°;$$

and (6) sequentially changing the coordinate values x and y of the matrix unit (x, y) and its corresponding intensities $I_1(x, y)$, $I_2(x, y)$, $I_3(x, y)$ and $I_4(x, y)$, and repeating step (5), and when the entire matrix units of the measuring sample are calculated, its phase retardation distribution and the fast axis azimuth angle distribution are obtained.

\* \* \* \* \*